United States Patent [19]

Tyo

[11] Patent Number: 4,696,291

[45] Date of Patent: Sep. 29, 1987

[54] PELVIC STABILIZATION DEVICE

[76] Inventor: James H. Tyo, 633 E. Walnut St., Green Bay, Wis. 54301

[21] Appl. No.: 837,025

[22] Filed: Mar. 6, 1986

[51] Int. Cl.$^4$ .............................................. A61F 5/02
[52] U.S. Cl. ........................................ 128/78; 128/69
[58] Field of Search ....................... 128/69, 78, 578 R

[56] References Cited

U.S. PATENT DOCUMENTS

| | | | |
|---|---|---|---|
| 1,983,829 | 12/1934 | Ziminski | 128/78 |
| 1,995,002 | 3/1935 | Lee | 128/78 |
| 2,320,183 | 5/1943 | Jungemann | 128/78 |
| 2,409,381 | 10/1946 | Pease, Jr. | 128/78 |
| 2,552,474 | 5/1951 | Austlid | 128/78 |
| 2,813,526 | 11/1957 | Beebe | 128/78 |
| 3,605,731 | 9/1971 | Tigges | 128/78 |
| 3,926,183 | 12/1975 | Spiro | 128/78 |
| 4,508,110 | 4/1985 | Modglin | 128/78 |
| 4,572,167 | 2/1986 | Brunswick | 128/78 |
| 4,576,154 | 3/1986 | Hyman et al. | 128/78 |

FOREIGN PATENT DOCUMENTS

| | | | |
|---|---|---|---|
| 1921306 | 10/1970 | Fed. Rep. of Germany | 128/78 |
| 275001 | 6/1930 | Italy | 128/78 |

Primary Examiner—Edgar S. Burr
Assistant Examiner—Tonya Lamb
Attorney, Agent, or Firm—Recka Joannes and Faller

[57] ABSTRACT

Device and method for treating low back pain comprising three generally rigid chemically inert members, which apply a centrally directed force to the abdomen and to the gluteal muscles; the three members are connected across the front of the pelvis by flexible connectors positioned above and below the anterior superior iliac spines.

10 Claims, 7 Drawing Figures

PELVIC STABILIZATION DEVICE

BACKGROUND OF INVENTION

1. Field of Invention

The device is a support which stabilizes the sacroiliac joints and increases intra-abdominal hydrostatic pressure, to relieve low back pain.

2. Description of the Related Art

Prior art devices used to limit motion of the pelvis and sacroiliac joints to relieve back pain, include elasticized fabric sacroiliac support belts as shown in Fritsch, U.S. Pat. No. 2,117,309, and in Nelkin, U.S. Pat. No. 3,096,760, and corsets, as are shown in Flaherty, U.S. Pat. No. 2,219,475, and in Johnson, U.S. Pat. No. 3,717,143.

A weighted belt exerting a counter moment to the weight of the viscera to alleviate back pain is shown in Bernston, U.S. Pat. No. 3,888,245.

The invention comprises three rigid members used to apply force to the abdomen to increase intra-abdominal hydrostatic pressure, and to the gluteal muscles to effectively shorten the gluteals, correcting improper pelvic tilt and locking the ilia and sacral joints.

It is an object of the invention to use the locking properties of the interdigitating ilia and sacral joints to limit pelvic movement.

The described invention eliminates fabric belts and their cleaning problems by using rigid plastic members. It is an object of the invention to eliminate pressure on sacral nerves by bridging the sacrum. It is an object of the invention to eliminate the irritation caused by pressure of elasticized belts on the bones of the pelvis which irritates the skin over the bones.

Elasticized belts exert a lateral force, normal to the anterior superior iliac spines, tending to wedge open the sacroiliac joints. It is an object of this invention to eliminate that force. The anterior superior iliac spines are bridged by the invention, by mounting straps above and below the anterior superior iliac spine. Such bridging eliminates the wedging force and allows increased intra abdominal hydrostatic pressure by mounting the abdomen force applying member within the anterior superior iliac spines.

DESCRIPTION OF THE PREFERRED EMBODIMENT

The sacroiliac joints transfer the weight of the torso to the legs. The joint is a stiff interdigitating joint. When a weight is carried or a vertical load is applied to the joint, ligaments pull the joint tightly together. The ligaments joining the ilia and sacral joints are shaped so as to increase rigidity with increasing loads.

Figure 1:
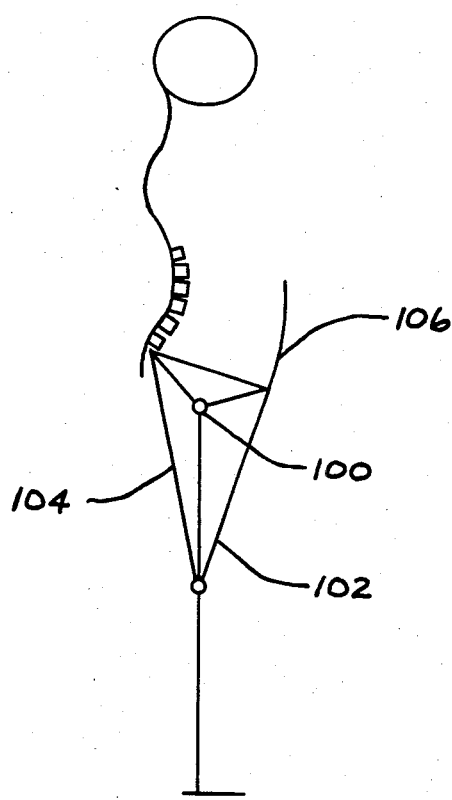
FIG. 1 is a schematic showing pelvic tilt around the trochanter, the quadriceps, the gluteal muscles, and the abdominal muscles.
Figure 3:
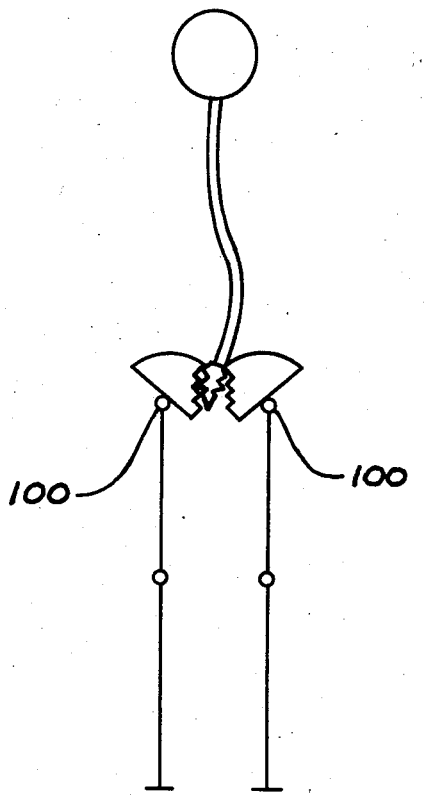
FIG. 3 is a schematic showing ilia and sacral joints loose, allowing lateral shift of the sacrum.

With chronic back muscle spasm or with menstruation, the joint loosens. Loosening of the joint allows an angular change of the sacrum, or increased pelvic tilt, or both, exacerbating pain. As the flexibility of the joint increases, pelvic tilt may increase as is shown in FIG. 1. Asymmetrical angle of the sacrum may increase as is shown in FIG. 3. As flexibility and asymmetry increases, so does back pain. This device is used to treat back pain when such pain is incident to looseness of the sacroiliac joints.

Prior art devices such as elasticized fabric belts and corsets alleviate pain by immobilizing the lumbar spine.

The uniform circumferential force applied by a sacroiliac belt causes problems. Belts apply force to the thinly covered bones of the pelvis causing irritation. The lateral force exerted centrally by the belts, normal to the pelvic crests, cause the pelvic crests to act as moment arms, forcing the pelvic crests towards each other and urging the sacroiliac joints at the base of the back bone open, stressing the joints. In prior art devices this moment is countered by a sacral pad which bears on the lower end of the backbone. Pads irritate the sacral nerves located below the pad.

Sacroiliac belts tend to ride up. Fabric also irritates the skin because of close contact and the fabric of belts and corsets becomes soiled by body fluids.

The device shown applies force to the gluteals, or buttocks, and to the abdomen through three non-fabric, bearing members. The members are generally rigid and can be easily washed.

Figure 2:
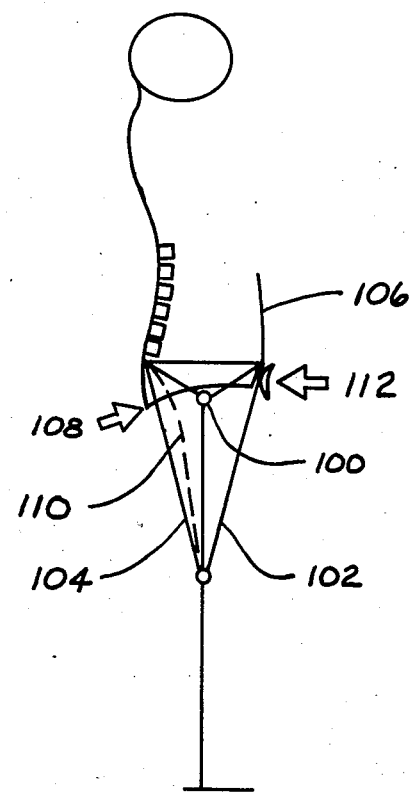
FIG. 2 is a schematic showing proper pelvic tilt, effected by exerting an anterior to posterior force to the abdomen, and at the same time exerting posterior to medial forces on both gluteals, effectively shortening the gluteal muscles, and increasing intra-abdominal hydrostatic pressure.

For purposes of illustration, FIG. 1 shows pelvis pivoted around the trochanter 100. FIG. 2 is provided to show how the device works. The FIGS. 1 and 2 can be analyzed as force diagrams. Quadriceps 102 and gluteals/hamstrings 104 act as large elastic bands which exert tension, pulling on the pivoting pelvis, rotating the pelvis around the trochanters.

The pelvis is rotated in a clockwise direction due to shortening of the quadriceps, caused by decreased muscle tone of the abdomen muscles 106 and gluteals.

If gluteals hamstrings 104, and quadriceps 102 and abdominal muscles 106 are in balance, correct pelvic tilt is as shown in FIG. 2.

Force 108 on gluteals effectively shortens gluteals, as shown by dotted line 110.

Shortening the gluteals has the same effect as shortening an elastic band by pulling it tighter. The increased force overrides the force of the quadriceps pivoting the pelvis counterclockwise.

Force on the abdomen 112 effectively shortens the abdominal muscles, lengthening the quadriceps. Hydrostatic pressure created by force 112 increases rigidity of the abdominal cavity providing support for the L5/S1 lumbar disc.

Figure 4:
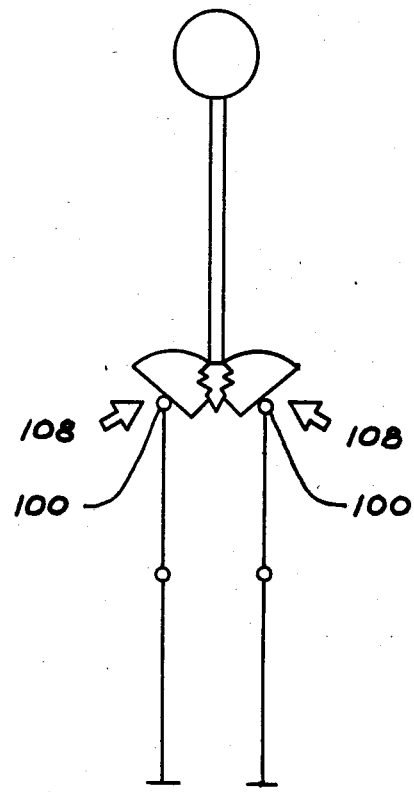
FIG. 4 is a schematic showing the pelvis stabilized with the sacroiliac joints locked.

The effect of the device on the sacroiliac joints is shown in FIG. 4. FIG. 3 shows the ilia and sacral joints prior to force 108 being applied. FIG. 4 shows the effect of force 108 in locking the ilia and sacral joints.

Figure 5:
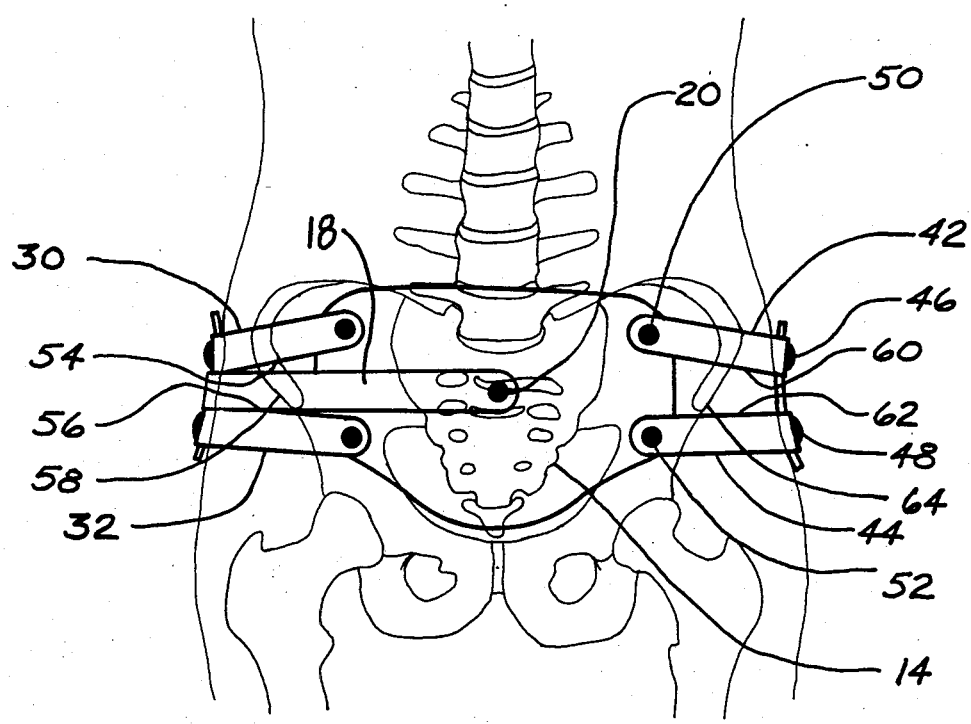
FIG. 5 is a front view of the device showing the relationship of the device to the bony structure of the body.
Figure 6:
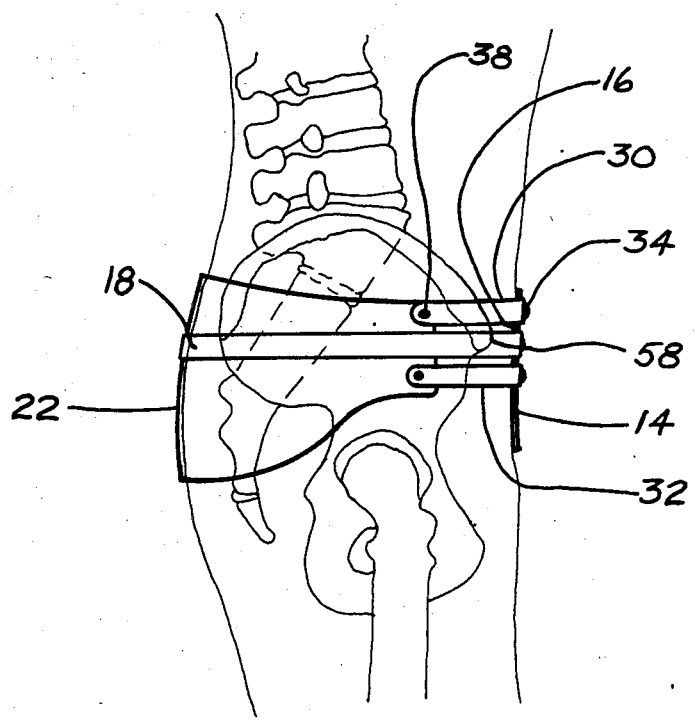
FIG. 6 is a side view of the device showing location of the device on a patient and the relationship of bony structure.

The pelvic stabilization device is shown on a patient in FIG. 5 and in FIG. 6.

The device comprises the following parts:
Anterior force applying member: 14
Anterior force applying member bearing surface: 16
Tension adjustment strap: 18
Strap attachment rivet: 20
Right posterior force applying member: 22
Right posterior force applying member bearing surface: 24
Left posterior force applying member: 26
Left posterior force applying member bearing surface: 28
Top connecting strap, anterior member to right posterior member: 30
Bottom connecting strap anterior member to right posterior member: 32
Pivot mount to anterior member top strap: 34
Pivot mount to anterior member bottom strap: 36
Pivot mount to right posterior member top strap: 38
Pivot mount to right posterior member bottom strap: 40
Top connecting strap: 42
Bottom connecting strap: 44
Pivot mount to anterior member top strap: 46
Pivot mount to anterior member bottom strap: 48
Pivot mount to left posterior member top strap: 50
Pivot mount to left posterior member bottom strap: 52
Lower surface of strap 30: 54
Upper surface of strap 32: 56
Right ASIS (anterior superior iliac spine): 58
Lower surface of strap 42: 60
Upper surface of strap 44: 62
Left ASIS: 64
Tensioning string connecting posterior plates: 66
Sacral nerve bridge: 68

Figure 7:
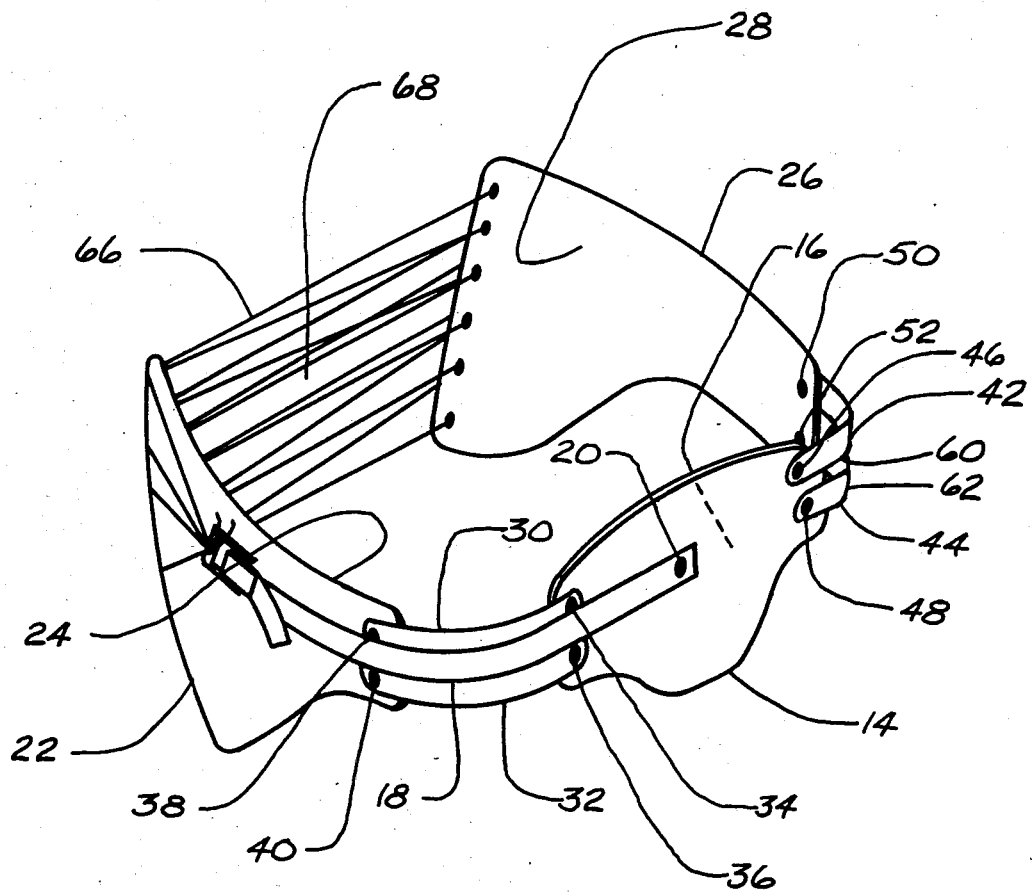
FIG. 7 is an isometric view of the device showing the generally rigid force applying members, flexible connectors and tensioning means.

The pelvic stabilization device 12 in FIG. 7 comprises an anterior force applying member 14. Bearing surface 16, of the member applies an anterior to posterior force to the area of the abdomen bordered by the symphysis pubis distally and by the anterior superior iliac spines laterally, as shown in FIG. 5 and in FIG. 6. This force increases hydrostatic pressure in the abdomen. Increased hydrostatic pressure increases the stability of the vertebral bodies, decreases loading on intervetebral discs and straightens up the torso. A tension adjusting strap 18 is connected to member 14 by rivet 20 as can best be seen in FIG. 7.

An anterior to medial force is applied at the right gluteal by member 22, through bearing surface 24 as is shown in FIG. 7. This force effectively shortens the gluteal as shown in FIG. 2, shortening the effective length of the muscle and rotating the pelvis, decreasing the sacral angle. An anterior to medial force is applied at the left gluteal by member 26 by bearing surface 28, decreasing the sacral angle as described above.

Posterior member 22 is connected to anterior member 14 by flexible straps 30 and 32 as can best be seen in FIG. 6. The flexible straps are pivotally mounted to the bearing members by pivot mounts 34, 36, 38 and 40. The pivotal mounting of the plates together with the flexibility of the straps allows the device to accommodate the shapes of different size patients without a change in the size of the three principal members.

Force is applied by tightening tensioning strings 66 which tie together the posterior plates as shown in FIG. 7.

Posterior member 26 is connected to pelvic member 14 by flexible straps 42 and 44. These straps are also pivotally mounted by pivot mounts 46, 48, 50, and 52 as best seen in FIG. 7.

Straps 30 and 42 are positioned above the anterior superior iliac spine 58 and 64. The anterior superior iliac spine is the bony protuberance felt at the front of the pelvis. The right anterior superior iliac spine is retained between the lower edges 54 of the top connecting strap 30; and the upper edges 56 of the bottom connecting strap 32; on the left between the upper and lower edges of straps 42 and 44. Location of the straps above and below the ASIS 58 can best be seen in FIG. 5.

Bottom connecting straps 32 and 44 are positioned to lie below the anterior superior iliac spine. The positioning of the straps above and below the anterior superior iliac spine prevents the device from riding up. By positioning the device with straps above and below the anterior superior iliac spins, no load bearing member bears on the thinly padded bones of the pelvis. The posterior bearing members 22 and 26 are also slightly cupped as can be seen in FIG. 7 to prevent riding up.

As can be seen on FIG. 7 no part of the device bears on the sacrum. The device bridges the sacrum 68 as shown in FIG. 7.

BEST METHOD

The device accommodates different sized patients, using three standard sized rigid members by varying the lengths of the connecting straps.

One standard size anterior member is used. The dimensions of this member were developed empirically by measuring several hundred adults of both sexes and by making plaster models of one hundred and fifty adults. The dimensions are such as to allow the abdomen plate to fit between the ASIS and the symphysis pubis of the great majority of patients.

The dimensions of and contours of the left and right gluteal members were developed from the same models.

Dimensions were determined fo the semirigid members to fit 95 percent of adult patients of both sexes. The abdomen plate in the current model has a width of 165 mm, a height of 115 mm, and a concave radius of 900 mm. The gluteal members are 160 mm wide, by 135 mm at maximum depth with an internal radius of 750 mm.

Fit of the device is not affected as much by the size of the suspended viscera as would be expected, because the abdominal member is mounted at the lowest part of the abdomen and is a compressive member. Contour to the gluteals is accommodated by varying the relationship of the upper and lower attachment straps.

Circumferential adjustment and the relative angles of the bearing members is effected by varying the length of the connecting straps.

Fitting the device to a patient comprises the following steps:

1. Measuring the circumference of the patient at a level just superior to the ASIS, substracting a predetermined number from that circumference (the number representing the circumference of the force applying members and the ties), and dividing the resultant number by two to determine the upper strap length.

2. Assembling the device with the upper straps attached.

3. Locating the device with the upper strap above the ASIS and the superior border of the gluteal plates at or below the level of the posterior superior iliac spines. That level is a landmark which is easily definable.

4. Applying force to the three bearing members to get close contact to the body, then measuring the length of the lower connecting straps necessary to span the distance between mounting hole in the anterior member and the mounting hole in the posterior member.

5. Attaching the bottom connecting straps.

The present device is made of polypropolene which is chemically insensitive to human skin, does not adhere to the skin and is not adhered to, dissolved by, or reactive to body fluid and common cleaning preparations. The bearing plates are made from a one-eighth inch semirigid polypropelene sheet and are heat formed into a shape conforming to the proper shape to apply pressure to the gluteals (specific dimensions being stated under Best Method). The anterior bearing member is heat formed to the proper shape to apply pressure to the abdomen. The straps are made of flexible one sixteenth inch polypropelene. High density polyethelene and formed nylon may be used. Production devices will be injection molded.

Any semirigid material insensitive to human skin and not adhered to or soluble in or reactive to body fluids or cleaning solutions may be used to make the bearing surfaces of the force applying members. Rigid plates such as stainless steel can be used. Preferably a low heat conductance should be used for comfort. No problem is caused by completely rigid bearing members. As rigidity decreases, the device becomes similar to an elasticized or fabric sacroiliac belt, except for the interior mounting of the abdomen member and the bridging of both ASIS and the sacrum.

Treatment over a period of months allows the sacral joints, relieved of the deforming force, to tighten and heal. The quadriceps regain length to effect normal pelvic position.

I claim:

1. A pelvic stabilization device comprising:
   a substantially rigid abdomen plate mounted between the symphsis pubis distally and the anterior superior iliac spines laterally operable to compress the abdomen between the symphsis pubis distally and the anterior superior iliac spines laterally;
   a first substantially rigid gluteal member operable to compress the right gluteal;
   a second substantially rigid gluteal member, operable to compress the left gluteal; the skin contact surface of such abdomen plate and gluteal plates being made of a material insensitive to human skin, insoluble in and non-reactive to body fluids and cleaning solutions;
   straps connecting the abdomen plate to each gluteal member;
   a tension adjustment strap affixed to the abdomen plate and to the gluteal members;
   a fastener operable to secure the tension adjustment strap.

2. The device in claim 1 wherein the tension adjustment strap comprises:
   a strap having two ends, one end of such strap being affixed to the abdomen plate, the other end of such strap being connected to the gluteal members such connection to the gluteal members bridging the sacrum;
   locking means comprising a buckle operable to secure the strap when tightened, thereby retaining a uniform pressure on the bearing members.

3. The device as in claim 1 wherein the substantially rigid abdomen plate is 165 millimeters wide, 115 milimeters high and has a concave radius of 900 millimeters.

4. The device as in claim 3 wherein said substantially rigid abdomen plate and the substantially rigid gluteal members are made of an unpadded sheet of a formed material selected from polypropolene, high density polyethelene and nylon.

5. The device as in claim 1 wherein the straps connecting the abdomen plate to each gluteal plate are made of a flexible material selected from polypropolene, high density polyethelene and nylon.

6. The straps as in claim 5 wherein such straps further comprise a first pair of straps connecting the substantially rigid abdomen plate to the substantially rigid gluteal members, mounted below the anterior superior iliac spine and a second pair of straps mounted above the anterior superior iliac spine, whereby the anterior superior iliac spines are bridged eliminating pressure on that thinly padded area of the pelvis and preventing the device from sliding up or down on the body.

7. The device as in claim 5 wherein the straps are pivotally mounted to the substantially rigid abdomen plate.

8. The device as in claim 5 wherein the straps are pivotally mounted to both abdomen plate and gluteal members.

9. The device as in claim 5 wherein the straps are pivotally mounted to both abdomen plate and gluteal members.

10. A pelvic stabilization device of the type in which a member dimensioned to encircle the pelvic region of the human body, to limit movement of the pelvis, is placed around the body, wherein the improvement comprises:
    a substantially rigid abdomen plate mounted on the surface of the abdomen, bearing on the pelvic area between the symphisis pubis distally and the anterior superior iliac spines laterally, operable to apply force to the abdomen within the area defined by the symphisis pubis distally and the anterior superior iliac spines laterally; such member generally conforming to the shape of the abdomen;
    a first substantially rigid gluteal member generally conforming to the shape of the right gluteal;
    a second substantially rigid gluteal member generally conforming to the shape of the left gluteal;
    such substantially rigid abdomen plate and gluteal members being made of an unpadded sheet of a material chosen from polypropolene, high density polyethelene and nylon;
    flexible straps, connecting the abdomen plate and the gluteal members, such straps positioned above and below the anterior superior iliac spines;
    a tension adjustment strap having two ends, one end of the strap being affixed to the abdomen plate, the other end of such strap being connected to the gluteal members, such connection to the gluteal members bridging the sacrum.

* * * * *